US012285545B2

(12) United States Patent
Taboas et al.

(10) Patent No.: US 12,285,545 B2
(45) Date of Patent: Apr. 29, 2025

(54) REGENERATION OF VITAL TOOTH PULP

(71) Applicant: University of Pittsburgh—Of the Commonwealth System of Higher Education, Pittsburgh, PA (US)

(72) Inventors: Juan M. Taboas, Pittsburgh, PA (US); Herbert L. Ray, Leechburg, PA (US); Jingming Chen, Pittsburgh, PA (US); Patrick Eugene Donnelly, Pittsburgh, PA (US); Tyler Swenson, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/979,038

(22) PCT Filed: Mar. 20, 2019

(86) PCT No.: PCT/US2019/023132
§ 371 (c)(1),
(2) Date: Sep. 8, 2020

(87) PCT Pub. No.: WO2019/183201
PCT Pub. Date: Sep. 26, 2019

(65) Prior Publication Data
US 2020/0405916 A1    Dec. 31, 2020

Related U.S. Application Data

(60) Provisional application No. 62/645,364, filed on Mar. 20, 2018.

(51) Int. Cl.
*A61L 27/52*    (2006.01)
*A61L 27/48*    (2006.01)
(Continued)

(52) U.S. Cl.
CPC .............. *A61L 27/52* (2013.01); *A61L 27/48* (2013.01); *A61L 27/54* (2013.01); *A61L 27/56* (2013.01);
(Continued)

(58) Field of Classification Search
CPC .......... A61L 27/52; A61L 27/44; A61L 27/54; A61L 27/56; A61L 27/58; A61L 1243/12; A61L 1230/414
See application file for complete search history.

(56) References Cited

U.S. PATENT DOCUMENTS 6,632,457 B1    10/2003    Sawhney
7,574,261 B2    8/2009    Dodge et al.
(Continued)

FOREIGN PATENT DOCUMENTS

CN    104548212    4/2015
CN    104307049 B    4/2016
(Continued)

OTHER PUBLICATIONS

The American Society of Hematology (a clinical and scientific hematology research institution) [online]. [retrieved Dec. 21, 2023]. https://ashpublications.org/blood/article/123/7/947/105650/The-dual-face-of-heparin-in-severe-infection (Year: 2014).*
(Continued)

*Primary Examiner* — Robert A Wax
(74) *Attorney, Agent, or Firm* — Klarquist Sparkman, LLP

(57) ABSTRACT

Methods of regenerating vital tooth tissue in situ after endodontic therapy include introducing a hydrogel scaffold into a root canal of a tooth in a patient after native pulp has been removed from the root canal. The hydrogel scaffold may comprise a sponge scaffold, and can be acellular. The hydrogel scaffold can contain chemotactic, angiogenic, neu-
(Continued)

rogenic, and/or immunomodulatory biofactors that cause infiltration of endogenous cells from the patient into the root canal. Alternatively, such biofactors/drugs can be administered to the patient separately from the hydrogel scaffold. The hydrogel scaffold can fill the periapical space of an abscessed root.

18 Claims, 12 Drawing Sheets

(51) Int. Cl.
    *A61L 27/54*     (2006.01)
    *A61L 27/56*     (2006.01)
(52) U.S. Cl.
    CPC ..... *A61L 2300/222* (2013.01); *A61L 2300/41* (2013.01); *A61L 2300/414* (2013.01); *A61L 2300/426* (2013.01); *A61L 2400/06* (2013.01); *A61L 2430/12* (2013.01)

(56) References Cited

U.S. PATENT DOCUMENTS

| | | | |
|---|---|---|---|
| 7,680,542 | B2 | 3/2010 | Widmann |
| 8,268,344 | B2 | 9/2012 | Ma et al. |
| 8,337,873 | B2 | 12/2012 | Mao |
| 8,920,791 | B2 | 12/2014 | Nakashima et al. |
| 9,040,070 | B2 | 5/2015 | Okamoto et al. |
| 9,180,072 | B2 | 11/2015 | Shah et al. |
| 9,180,166 | B2 | 11/2015 | Arinzeh et al. |
| 9,228,027 | B2 * | 1/2016 | Gurtner ................ A61P 41/00 |
| 9,327,015 | B2 | 5/2016 | Serhan et al. |
| 9,724,368 | B2 * | 8/2017 | Nakashima ............ A61P 43/00 |
| 2007/0286880 | A1 | 12/2007 | Vasiliev et al. |
| 2009/0148486 | A1 | 6/2009 | Lu et al. |
| 2011/0172150 | A1 * | 7/2011 | Bader .................... A61P 13/02 514/7.7 |
| 2011/0177134 | A1 | 7/2011 | Harmon et al. |
| 2011/0274742 | A1 | 11/2011 | Arinzeh et al. |
| 2012/0209319 | A1 | 8/2012 | Bianco-Peled et al. |
| 2012/0214217 | A1 * | 8/2012 | Grogan ................ C12N 5/0655 435/325 |
| 2013/0052155 | A1 | 2/2013 | Marcolongo et al. |
| 2014/0112973 | A1 | 4/2014 | Steinberg et al. |
| 2014/0256843 | A1 | 9/2014 | Sender et al. |
| 2014/0302111 | A1 * | 10/2014 | Mao ........................ A61L 27/12 514/8.4 |
| 2014/0315805 | A1 | 10/2014 | Carmichael et al. |
| 2016/0038643 | A1 | 2/2016 | Detamore et al. |
| 2016/0095958 | A1 | 4/2016 | Grayson et al. |
| 2016/0296664 | A1 * | 10/2016 | Lu ......................... A61K 9/0024 |
| 2017/0203009 | A1 * | 7/2017 | Yang ....................... A61L 27/18 |
| 2019/0048151 | A1 | 2/2019 | Wang et al. |
| 2020/0205983 | A1 | 7/2020 | Vargas Diaz et al. |
| 2020/0306143 | A1 * | 10/2020 | Yelick ................ A61L 27/3808 |
| 2021/0213170 | A1 | 7/2021 | Taboas et al. |
| 2021/0283311 | A1 * | 9/2021 | Bertassoni ............. A61L 27/52 |

FOREIGN PATENT DOCUMENTS

| | | |
|---|---|---|
| EP | 2268254 | 1/2011 |
| EP | 2460529 | 6/2012 |
| JP | 2005-211477 A | 8/2005 |
| JP | 2005-213449 A | 8/2005 |
| JP | 5748194 B2 | 7/2015 |
| WO | WO 2009/078971 | 6/2009 |
| WO | WO 2010/148229 | 12/2010 |
| WO | WO 2012/069870 | 5/2012 |
| WO | WO 2011/048803 A1 | 3/2013 |
| WO | WO2013/171736 A1 | 11/2013 |
| WO | WO2014/169236 A1 | 10/2014 |
| WO | WO 2015/168292 A1 | 11/2015 |
| WO | WO 2016/011039 | 1/2016 |
| WO | WO2017/152112 A2 | 9/2017 |
| WO | WO2019/094389 A1 | 5/2019 |
| WO | WO2019/183201 A1 | 9/2019 |
| WO | WO2019/241577 A1 | 12/2019 |

OTHER PUBLICATIONS

National Library of Medicine (The United States National Library of Medicine) [online]. [retrieved Dec. 21, 2023]. https://www.ncbi.nlm.nih.gov/pmc/articles/PMC3074524/ (Year: 2009).*
Extended Search Report for related European Application No. 19771745.7, 9 pages, dated Nov. 19, 2021.
Ishimatsu et al., "Formation of Dentinal Bridge on Surface of Regenerated Dental Pulp in Dentin Defects by Controlled Release of Fibroblast Growth Factor-2 From Gelatin Hydrogels," *JOE*, 35(6):858-865 (Jun. 6, 2009).
Chrepa, et al., "Evaluation of a Commercially Available Hyaluronic Acid Hydrogel (Restylane) as Injectable Scaffold for Dental Pulp Regeneration: An In Vitro Evaluation," *Journal of Endodontics*, 43(2):257-262 (Feb. 2017).
Diogenes, et al., "Regenerative Endodontic Procedures: Clinical Outcomes," *Dental Clinics of North America*, 61(1):111-125 (Jan. 2017).
Fayazi, et al., "Comparative Evaluation of Chemotactic Factor Effect on Migration and Differentiation of Stem Cells of the Apical Papilla," *Journal of Endodontics*, 43(8):1288-1293 (Aug. 2017).
Galler, et al., "Cell-free Approaches for Dental Pulp Tissue Engineering," *Journal of Endodontics*, 40(4): S41-S45 (Apr. 2014).
Iohara et al., "Complete Pulp Regeneration After Pulpectomy by Transplantation of CD105+ Stem Cells with Stromal Cell-Derived Factor-1," *Tissue Engineering: Part A*, 17(15-16):1911-1920 (Mar. 2011).
Prescott, et al., "In Vivo Generation of Dental Pulp-like Tissue by Using Dental Pulp Stem Cells, a Collagen Scaffold, and Dentin Matrix Protein 1 after Subcutaneous Transplantation in Mice," *Journal of Endodontics*, 34(4):421-426 (May 2008).
Song, et al., "Decellularized Human Dental Pulp as a Scaffold for Regenerative Endodontics," *Journal of Dental Research*, 96(6):640-646 (Feb. 14, 2017).
Tan et al., "Regeneration of dentin-pulp-like tissue using an injectable tissue engineering technique," *RSC Advances*, 5(73):59723-59737 (Jun. 23, 2015).
Viswanath, A., et al., "Extracellular matrix-derived hydrogels for dental stem cell delivery," J Biomed Mater Res A 105(1): 319-328 (Nov. 5, 2016).
Li, et al., "Pulp regeneration in a full-length human tooth root using a hierarchical nanofibrous microsphere system," *Acta Biomaterialia*, 35: 57-67 (Apr. 15, 2016).
Neves, et al., "Promotion of natural tooth repair by small molecule GSK3 antagonists," *Scientific Reports*, 7(39654), 7 pages (Jan. 9, 2017).
Palma, et al., "Histologic Evaluation of Regenerative Endodontic Procedures with the Use of Chitosan Scaffolds in Immature Dog Teeth with Apical Periodontitis," *Journal of Endodontics*, 43(8):1279-1287 (Mar. 2017).
Qu, et al., "Complete pulpodentin complex regeneration by modulating the stiffness of biomimetic matrix," *Acta Biomaterialia*, 16:60-70 (Jan. 2015).
Sonoyama, et al., "Mesenchymal Stem Cell-Mediated Functional Tooth Regeneration in Swine," *PLoS ONE*, 1(e79) 9 pages (Dec. 2006).
Ehrmann et al. "The relationship of intracanal medicaments to postoperative pain in endodontics," *International Endodontic Journal* 36: 868-875 (2003).
Ishimatsu et al., "Formation of dentinal bridge on surface of regenerated dental pulp in dentin defects by controlled release of fibroblast growth factor=2 from gelatin hydrogels," *J. Endod.* 35(6): 858-865 (Jun. 2009).
Kim et al., "Regeneration of dental-pulp-like tissue by chemotaxis-induced cell homing," *Tissue Engineering* Part A, 16(10): 3023-3031 (Nov. 10, 2010).

(56) References Cited

OTHER PUBLICATIONS

Chau, "Regulation of Growth Plate and Articular Chondrocyte Differentiation: Implications for Longitudinal Bone Growth and Articular Cartilage Formation," Karolinska Institutet, Stockholm, May 16, 2014 (68 pages).

Chen, et al., "Hydrogel to guide chondrogenesis versus osteogenesis of mesenchymal stem cells for fabrication of cartilaginous tissues," *Biomed. Mater.*, 15:4, Sections 2.2, 2.4, 5, p. 9 (right column), May 8, 2020 (10 pages).

Huebsch, et al., "Ultrasound-triggered disruption and self-healing of reversibly cross-linked hydrogels for drug delivery and enhanced chemotherapy," *PNAS*, 111.27: 9762-9767, Jul. 8, 2014.

International Search Report and Written Opinion for International Application No. PCT/US2017/020765, mailed by the Korean Searching Authority on Jun. 19, 2017 (12 pages).

International Search Report and Written Opinion for International Application No. PCT/US2019/037081, mailed by the Israeli Searching Authority on Oct. 10, 2019 (11 pages).

International Search Report and Written Opinion for International Application No. PCT/US2021/051096, mailed by the Israeli Searching Authority on Dec. 15, 2021 (11 pages).

Knipe and Peppas, "Multi-responsive hydrogels for drug delivery and tissue engineering applications," *Regenerative Biomaterials*, 1.1: 57-65, 2014.

Kwon and Han, "Chondroitin sulfate-based biomaterials for tissue engineering," *Turk J Biol.*, 40.2: 290-299, Feb. 23, 2016.

Nilsson, et al., "Gradients in bone morphogenetic protein-related gene expression across the growth plate," *Journal of Endocrinology*, 193:75-84, Jan. 19, 2007.

Phadke, et al., "Rapid self-healing hydrogels," *PNAS*, 109(12):4383-4388, Mar. 20, 2012.

Rutt, "Molecular Analysis of the Epiphyseal Growth Plate in Rachitic Broilers: Evidence for the Etiology of the Condition," Master's Thesis, The Ohio State University, 2008 (110 pages).

Santo, et al., "Controlled Release Strategies for Bone, Cartilage, and Osteochondral Engineering-Part 1: Recapitulation of Native Tissue Healing and Variables for the Design of Delivery Systems," *Tissue Engineering: Part B*, 19.4: 308-326, Aug. 19, 2013.

Spitters, et al., "A Dual Flow Bioreactor with Controlled Mechanical Stimulation for Cartilage Tissue Engineering," *Tissue Engineering: Part C*, 19.10, Aug. 2013 (10 pages).

Yu, et al., "Multifunctional Hydrogel with Good Structure Integrity, Self-Healing, and Tissue-Adhesive Property Formed by Combining Diels-Alder Click Reaction and Acylhydrazone Bond," *Applied Materials & Interfaces*, 7: 24023-24031, Oct. 23, 2015.

Athirasala et al., "A Novel Strategy to Engineer Pre-Vascularized Full-Length Dental Pulp-like Tissue Constructs," *Scientific Reports* 7:3323, Jun. 2017 (11 pages).

Saito et al., "Preparation of gelatin hydrogels incorporating low-molecular-weight heparin for anti-fibrotic therapy," *Acta Biomaterialia* 8(2):646-652, Oct. 2012.

Hinz, "The extracellular matrix and transforming growth factor-B1: Tale of a strained relationship," *Matrix Biol.* 47: 54-65, 2015.

Association AD, "AAE Clinical Considerations for a Regenerative Procedure, Revised Jun. 8, 16," American Dental Association; Chicago, IL, 2016 (10 pages).

Banchs and Trope, "Revascularization of Immature Permanent Teeth with Apical Periodontitis: New Treatment Protocol," *Journal of Endodontics* 30:196-200, Apr. 2004.

Bick and Frenkel, Clinical Aspects of Heparin-Induced Thrombocytopenia and Thrombosis and Other Side Effects of Heparin Therapy, *Clin. Appl. Thrombosis/Hemostasis* 5: S7-S15, 1999.

Bloemen et al., "Incidence(HIT) and diagnosis of heparin-induced thrombocyotpenia (HIT) in patients with traumatic injuries treated with unfractioned or low-molecular-weight heparin: A literature review," *Injury* 43: 548-52, May 2012.

Donnelly et al., "A Chorioallantoic Culture Model to Evaluate Pulp Regeneration Therapies," In Transactions of the AADR/CADR Annual Meeting & Exhibition, Fort. Lauderdale, FL, Mar. 24, 2018 (Abstract).

Donnelly et al., "A Chorioallantoic Culture Model to Evaluate Pulp Regeneration Therapies," *Journal of Endodontics*, Presented at the AAE Foundation 2018 Meeting, Denver, CO, Apr. 26, 2018 (Abstract).

Dregalla et al., "Red blood cells and their releasates compromise bone marrow-derived human mesenchymal stem/stromal cell survival in vitro," *Stem Cell Res Ther.* 12:547, 2021 (15 pages).

Everts et al., "Assessing clinical implications and perspectives of the pathophysiological effects of erythrocytes and plasma free hemoglobin in autologous biologics for use in musculoskeletal regenerative medicine therapies. A review," *Regenerative Therapy* 11:56-64, 2019.

Frimat et al., "Hemolysis Derived Products Toxicity and Endothelium: Model of the Second Hit," *Toxins* 11:660, 2019 (34 pages).

Kim et al., "Review: Regenerative endodontics: a comprehensive review," *International Endodontic Journal* 51:1367-88, 2018.

Martel et al., "Risk for heparin-induced thrombocytopenia with unfractionated and low-molecular-weight heparin thromboprophylaxis: a meta-analysis," *Blood* 106: 2710-2715, 2005.

Mohammadi, "Systemic and local applications of steroids in endodontics: an update review," *International Dental Journal* 59: 297-304, 2009.

Taboas et al., "Acellular hydrogel regenerates a vascularized tissue producing organized mineral along the instrumented canal wall," Pulp Biology and Regeneration Group Satellite Meeting: Basic and Translational Research in Pulp Biology—Developing Technologies for Regenerating Vital Dental Tissues, Portland, OR, Jun. 2019 (Poster).

Zaky et al., "Effect of the Periapical 'Inflammatory Plug' on Dental Pulp Regeneration: A Histologic In Vivo Study," *J Endod.* 46:51-56, 2020.

Bernstein et al., " Can Bone Healing in Distraction Osteogenesis Be Accelerated by Local Application of IGF-1 and TGF-Beta1?" *J Biomed Mater Res Part B Appl Biomater.* 92.1: 215-225, 2010.

Bonewald and Mundy, "Section III: Basic Science and Pathology: Role of Transforming Growth Factor-Beta in Bone Remodeling," *Clinical Orthopaedics and Related Research* 250: 261-276, Jan. 1990.

Bostrom and Asnis, "Transforming Growth Factor Beta in Fracture Repair," *Clinical Orthopaedics and Related Research* 355S: S124-S131, 1998.

Ehrhart et al., "Effect of Transforming Growth Factor-Beta1 on Bone Regeneration in Critical-Sized Bone Defects after Irradiation of Host Tissues," *Am J Vet Res.* 66.6: 1039-1045, 2005.

Einhorn and Gerstenfeld, "Fracture Healing: Mechanisms and Interventions," *Nat Rev Rheumatol.* 11.1: 45-54, Jan. 2015.

Ekegren et al., "Incidence, Costs and Predictors of Non-Union, Delayed Union and Mal-Union Following Long Bone Fracture," *Int J Environ Res. Public Health* 15.12: 2845, 2018.

Gao et al., "Advances in Animal Models for Studying Bone Fracture Healing," *Bioengineering* (Basel) 10: 201, 2023 (18 pages).

Giannoudis et al., "Autologous Bone Graft: When Shall We Add Growth Factors?" *Foot Ankle Clin.* 15.4: 597-609, 2010.

Heckman et al., "Bone Morphogenetic Protein but Not Transforming Growth Factor-Beta Enhances Bone Formation in Canine Diaphyseal Nonunions Implanted with a Biodegradable Composite Polymer," *J Bone Joint Surg Am.* 81.12: 1717- 1729, Dec. 1999.

Hettiaratchi et al., "Enhanced in Vivo Retention of Low Dose BMP-2 via Heparin Microparticle Delivery Does Not Accelerate Bone Healing in a Critically Sized Femoral Defect," *Acta Biomater.* 59: 21-32, 2017.

Ho-Shui-Ling et al., "Bone Regeneration Strategies: Engineered Scaffolds, Bioactive Molecules and Stem Cells Current Stage and Future Perspectives," *Biomaterials* 180: 143-162, Oct. 2018.

Janssens et al., "Transforming Growth Factor-Beta1 to the Bone," *Endocr Rev.* 26.6: 743-774, 2005.

Katagiri et al., "Bone morphogenetic protein-induced heterotopic bone formation: What have we learned from the history of a half century," *Japanese Dental Science Review* 51: 42-50, 2015.

(56) References Cited

OTHER PUBLICATIONS

Kaur et al., "A segmental defect adaptation of the mouse closed femur fracture model for the analysis of severely impaired bone healing," Animal Model Exp Med. 3: 130-139, 2020.
Lind et al., "Transforming Growth Factor-Beta-6 Stimulates Bone Ongrowth. Hydroxyapatite-Coated Implants Studied in Dogs," Acta Orthop Scand. 67.6: 611- 616, 1996.
Lind et al., "Transforming Growth Factor-Beta 1 Stimulates Bone Ongrowth to Weight-Loaded Tricalcium Phosphate Coated Implants: An Experimental Study in Dogs," J Bone Joint Surg Br. 78B.3: 377-382, May 1996.
Lind et al., "Transforming Growth Factor-Beta1 Adsorbed to Tricalciumphosphate Coated Implants Increases Peri-Implant Bone Remodeling," Biomaterials 22.3: 189-193, Feb. 2001.
Matsuura et al., "Distinct Characteristics of Mandibular Bone Collagen Relative to Long Bone Collagen: Relevance to Clinical Dentistry," Biomed Res Int. 2014: 769414, 2014 (9 pages).
Moses et al., "The Discovery and Early Days of Tgf-B: A Historical Perspective," Cold Spring Harb Perspect Biol. 8.7: a021865, 2016 (28 pages).
Moxham et al., "TGF-Beta 1 Forms Functionally Normal Bone in a Segmental Sheep Tibial Diaphyseal Defect," J Otolaryngol 25.6: 388-392, 1996.
Nauth et al., "Critical-Size Bone Defects: Is There a Consensus for Diagnosis and Treatment?" J Orthop Trauma 32: S7-S11, Mar. 2018.
Nikolidakis et al., "Chapter 5: The Effect of a Low Dose of Transforming Growth Factor Beta1 (TGF-Beta1) on the Early Bone-Healing around Oral Implants Inserted in Trabecular Bone," Doctoral Thesis: Oral Implants: The Effect of Biological Factors on Bone Healing, Department of Periodontology and Biomaterials, Radboud University Nijmegen Medical Center, Nijmegen, The Netherlands, 69-83, 2009.
Olivos-Meza et al., "Pretreatment of Periosteum with TGF-Beta1 in Situ Enhances the Quality of Osteochondral Tissue Regenerated from Transplanted Periosteal Grafts in Adult Rabbits," Osteoarthritis and Cartilage 18.9: 1183-1191, Sep. 2020.
Poniatowski et al., "Transforming Growth Factor Beta Family: Insight into the Role of Growth Factors in Regulation of Fracture Healing Biology and Potential Clinical Applications," Mediators Inflamm. 2015: 137823, 2015 (17 pages).
Raschke et al., "Insulin-like Growth Factor-1 and Transforming Growth Factor-Beta1 Accelerates Osteotomy Healing Using Polylactide-Coated Implants as a Delivery System: A Biomechanical and Histological Study in Minipigs," Bone 30.1: 144-151, 2002.
Reyes et al., "Effect of Triple Growth Factor Controlled Delivery by a Brushite-PLGA System on a Bone Defect," Injury 43.3: 334-342, 2012.
Reyes et al., "Repair of an Osteochondral Defect by Sustained Delivery of BMP-2 or TGFß1 from a Bilayered Alginate-PLGA Scaffold," J Tissue Eng Regen Med. 8.7: 521-533, 2014.
Ripamonti et al., "Bone Induction by BMPs/OPs and Related Family Members in Primates," J Bone Joint Surg Am. 83A Suppl 1 (Pt. 2): S116-127, 2001.
Roddy et al., "Treatment of critical-sized bone defects: clinical and tissue engineering perspectives," Eur J Orthop Surg Traumatol. 28: 351-362, 2018.
Schlickewei et al., "Current and Future Concepts for the Treatment of Impaired Fracture Healing," Int J Mol Sci. 20.22: 5805, 2019 (26 pages).
Schouten et al., "Effects of Implant Geometry, Surface Properties, and TGF-Beta1 on Peri-Implant Bone Response: An Experimental Study in Goats," Clin Oral Implants Res. 20.4: 421-429, 2009.
Servin-Trujillo et al., "Use of a Graft of Demineralized Bone Matrix along with TGF-B1 Leads to an Early Bone Repair in Dogs," J Vet Med Sci. 73.9: 1151- 1161, 2011.

Sherris et al., "Mandibular Reconstruction with Transforming Growth Factor- Beta1," Laryngoscope 108.3: 368-372, 1998.
Shigeno et al., "Regenerative Repair of the Mandible Using a Collagen Sponge Containing TGF-Beta1," Int J Artif Organs. 25.11: 1095-102, Nov. 2002.
Stewart, "Fracture Non-Union: A Review of Clinical Challenges and Future Research Needs", Malays Orthop J. 13.2: 1-10, Jul. 2019.
Sun et al., "Role of Transforming Growth Factor Beta (TGF-Beta) in Repairing of Bone Defects," Chin Med Sci J. 11.4: 209-214, Dec. 1996.
Sun et al., "Evaluation of Transforming Growth Factor Beta and Bone Morphogenetic Protein Composite on Healing of Bone Defects," Chin Med J. 110.12: 927-931, 1997.
Sun et al., "Collagen-Hydroxyapatite/Tricalcium Phosphate Microspheres as a Delivery System for Recombinant Human Transforming Growth Factor-Beta 1," Artificial Organs 27.7: 605-612, 2003.
Szivek et al., "Transforming Growth Factor-Beta1 Accelerates Bone Bonding to a Blended Calcium Phosphate Ceramic Coating: A Dose-Response Study," J Biomed Mater Res A 68.3: 537-543, 2004.
Teixeira et al., "Skeletal tissue regeneration: where can hydrogels play a role?" International Orthopaedics (SICOT) 38: 1861-1876, 2014.
Wang et al., "Calvarial versus Long Bone: Implications for Tailoring Skeletal Tissue Engineering," Tissue Engineering: Part B 26.1: 46-63, 2020.
Zhang et al., "Advancements in Hydrogel-Based Drug Sustained Release Systems for Bone Tissue Engineering," Front Pharmacol. 11: 622, 2020 (13 pages).
Beck et al., "Rapid Publication TGF-$\beta_1$ Induces Bone Closure of Skull Defects," Journal of Bone and Mineral Research 6.11: 1257-1265, 1991.
Da Silva Feitosa et al., "Thyroid Hormones May Influence Cortical Bone Healing Around Titanium Implants: A Histometric Study in Rats," J Periodontol. 79.5: 881-887, 2008.
Daugaard et al., "The combined effect of parathyroid hormone and bone graft implant fixation," J Bone Joint Surg Br. 93.1: 131-139, Jan. 2011.
"Definitation of Layer", Google Search, printed Sep. 24, 2024 (1 page).
Faghihi et al., "The effect of purmorphamine and sirlimus on osteogenic differentiation of human bone marrow-derived mesenchymal stem cells," Biomedicine and Pharmacotherapy 67: 31-38, 2013.
Riederer et al., "Dual Delivery Biomaterial System for the Treatment of Growth Plate Injuries," Tissue Engineering—Part A 20, Suppl. 1, S-32, Abstract No. O-385, Meeting Info: 2014 TERMIS-AM Conference, Washington, DC (Dec. 13-16, 2014), Dec. 2014 (1 page).
Aufdemorte et al., "An Intraosseous Device for Studies of Bone-Healing," The Journal of Bone and Joint Surgery 74-A.8: 1153-1161, 1992.
Hoffman, "Hydrogels for biomedical applications," Adv Drug Deliv Rev. 54.1: 3-12, Jan. 2002.
Kaminski et al., "pH-Sensitive Genipin-Cross-Linked Chitosan Microspheres for Heparin Removal," Biomacromolecules 9: 3127-3132, 2008.
Lerner, "Transforming Growth Factor-$\beta$ Stimulates Bone Resorption in Neonatal Mouse Calvariae by a Prostaglandin-Unrelated but Cell Proliferation-Dependent Pathway," Journal of Bone and Mineral Research 11.11: 1628-1639, 1996.
Lind, "Growth factor stimulation of bone healing," Acta Orthopaedica Scandinavica 69:Sup 283: 1-37, 1998.
Sinha et al., "Chitosan microspheres as a potential carrier for drugs," International Journal of Pharmaceuticals 274: 1-33, 2004.
Sumner et al., "Enhancement of Bone Ingrowth by Transforming Growth Factor-$\beta$," The Journal of Bone and Joint Surgery 77-A.8: 1135-1147, Aug. 1995.

* cited by examiner

| | Dynamic Modulus (kPa) | Relaxation Modulus (kPa) |
|---|---|---|
| Hydrogel | 10-27 | 5-22 |
| Sponge (hydrated) | 8 | 10 |
| Sponge (dry) | $25 \times 10^6$ | |

REGENERATION OF VITAL TOOTH PULP

CROSS REFERENCE TO RELATED APPLICATIONS

This application is the U.S. National Stage of International Application No. PCT/US2019/023132, filed Mar. 20, 2019, which claims the benefit of U.S. Provisional Application No. 62/645,364 filed Mar. 20, 2018, which is incorporated by reference herein in its entirety.

ACKNOWLEDGMENT OF GOVERNMENT SUPPORT

This invention was made with government support under grant no. IIP-1149702 awarded by the NSF. The government has certain rights in the invention.

FIELD

This application concerns technologies for regeneration of vital tooth pulp, in particular as a therapy following root canal procedures.

BACKGROUND

Root canal treatment (RCT) is an endodontic procedure performed in dental clinics to repair teeth with infected pulp and periapical tissue. The goal in RCT is to prevent and heal apical periodontitis by eliminating inflamed or infected pulp, and to prevent bacterial contamination of the by obturating (filling) the void with inert materials (a sealer and filler). The tooth consists of a chamber in the crown (corona, top) and canals in the roots (radicula) through which blood vessels and nerves enter into the chamber. The tip of the roots is the apex and the periapical space is the tissue outside of the tooth root around the tip, consisting of periodontal ligament, bone, and marrow. During a root canal treatment, infected pulp is removed (coronal and/or radicular), the periapical space probed if necessary, and canals are irrigated with disinfectant solution. The disinfected canal space is shaped and filled with an inert material to prevent reinfection.

According to the American Dental Association survey of dental services, 15 million root canal treatments are performed in the U.S. every year. The average success rate of RCT is 70%. Acute RCT failures can be caused by persistence of bacteria in the canals and apex, inadequate or overextended root filling, improper coronal seal, untreated major and accessory canals, iatrogenic procedural errors, complications of instrumentation, and/or other reasons.

Among these failure reasons, persistence of bacteria and inadequate or overextended root filling are the foremost causes (>65%). Use of gutta-percha endodontic filling points (thereinafter refer to as gutta-percha), the most common conventional filler for root canal therapy, is inescapably correlated with these two causes. Gutta-percha is made of a bio-inert thermoplastic material consisting of 20% gutta-percha matrix (a latex elastomer derived from tree resin), 66% zinc oxide, 11% heavy metal sulfates, and 3% waxes and/or resins.

Long-term RCT failures can be caused by interrelated events such as bacterial re-infection, shrinkage of fillings, and failure of coronal seals. Again, the use of gutta-percha is correlated with these.

Gutta-percha contributes to root canal treatment failure essentially because it is a non-vital space filling material with no regenerative capacity. Vitality of the tooth pulp is important for long-term prognosis because it prevents bacterial infection and provides protective sensation. Living pulp tissue generates an outward interstitial fluid flow through the tubules that contributes to prevention of bacterial invasion into the tooth chamber. If infection does occur, vital tissue allows natural defensive actions of immune cells to clear out bacteria. In addition, vital tissue can sense discomfort or pain when the tooth experiences high load (for example biting on a small rock), so the biting action can be stopped in time to prevent tooth cracking. Gutta-percha cannot provide these protective properties of vital pulp tissue. In addition, gutta-percha shrinks over time, leaving gaps between the filler and canal walls that provide a conduit for bacterial invasion. It also is semi-rigid, requiring canal shaping and making it unable to fill complicated accessory roots which are often curled, resulting in the root prone for reinfection. Vital tissue is needed to maintain the natural immunological response, and to prevent bacterial infiltration through the dentin tubules, accessory canals, and failing coronal restorations.

When root canal treatment fails, endodontic retreatment is necessary to remove the infection. During the procedure, old fillers are removed, the canal space is redisinfect and then filled with new obturating material. Endodontic retreatment is prone to fail. Dentists typically advise to extract the tooth when retreatment failure occurs.

To increase success rate of first-time root canal treatment, alternative fillers have been developed. Resorbable fillers made from polyesters are available, but these are also subject to shrinkage and are much less popular with dentists. All these fillers undesirably require the use of sealers to reach voids between the filler and tooth canal walls.

Regenerative approaches have been proposed as an alternative to root canal treatment. Revascularization is one regenerative therapy for root canals. It consists of inducing bleeding in the periapical space (the tissue outside the root at its tip) by probing, which fills the root with blood. This clinical therapy does not employ any scaffold material or bio-factor. It is performed in children with some success because their teeth are still growing and have high healing potential. However, this approach is not suitable for young adults and older patients as their teeth are no longer growing. Outcomes of revascularization root canal treatment is poor in adults. Dentists are looking for a product to improve root canal treatment outcomes. Alternative investigational clinical approaches include filling with autologous platelet rich plasma, but results are poor and this therapy requires significant overhead for the practitioner in terms of training, equipment and licensing.

Alternative investigational approaches in animals include filling with combinations of biomaterials, cells, and drugs. However, pulpectomy, disinfection and periapical space probing elicit an inflammatory response in the periapical space that impairs tissue formation within the tooth. This is of greater impact for acellular therapy. These approaches do not address the need to guide the inflammatory response while promoting cellular migration into the tooth from the periapical space and vital tissue formation in the tooth.

SUMMARY

Disclose herein are implantable materials and methods for regeneration of vital tooth tissue within coronal and radicular chambers in situ after root canal therapy. After a root canal is treated, in some embodiments the canal is filled with an acellular material comprising a hydrogel scaffold and/or a sponge scaffold. In some methods, the hydrogel scaffold can contain chemotactic, angiogenic, neurogenic, and/or immunomodulatory biofactors that cause infiltration of endogenous cells from the patient into the root canal. In other methods, one or more of these biofactors or drugs can be absent from the hydrogel scaffold and separately administered to the patient. The disclosed technology can revitalize the tooth, regenerating living tissue in the root canal, including nerve tissue, vascular tissue, and other native tissue, saving the tooth and protecting the tooth from further damage.

The foregoing and other objects, features, and advantages of the disclosed technology will become more apparent from the following detailed description, which proceeds with reference to the accompanying figures.

BRIEF DESCRIPTION OF THE DRAWINGS

FIG. 6A is at 1 hour, FIG. 6B is at 24 hours. Green=live cells, Red=dead cells.

FIG. 17 shows sponges doped with buffered saline solution without cytokines/growth factors and cultured on the CAM for one week, while FIG. 18 shows sponges doped with saline solution containing cytokines/growth factors and cultured on the CAM for one week.

DETAILED DESCRIPTION

Figure 1A:
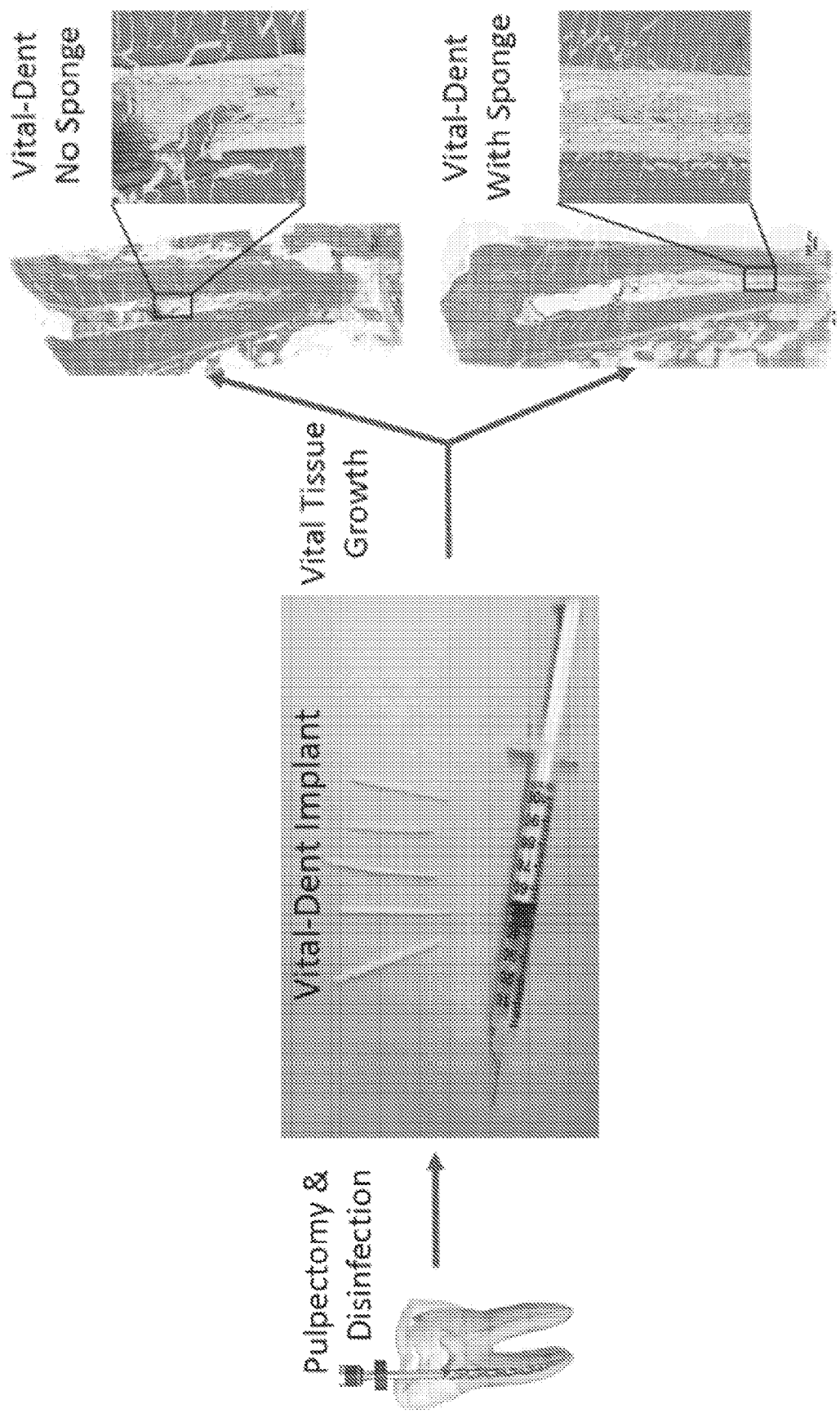
FIG. 1A illustrates methods disclosed herein for regeneration of vital tooth tissue within coronal and radicular chambers in situ after root canal therapy. The methods can include a pulpectomy and disinfection before implanting a hydrogel material with or without a sponge scaffold material.

The disclosed technology includes implantable materials and methods to regenerate vital tooth pulp in situ after endodontic therapy, or root canal therapy (RTC). Root canal treatments often result in re-infection and injury, which is why re-treatment usually ends with pulling the tooth. This is because the treated tooth is non-vital; it cannot sense/report reinfection and injury. No clinical method exists to revitalize teeth in adults. The disclosed materials and methods replace the conventional obturating (filler) material and promote formation of a living tissue in the treated tooth canal and chamber. A particular benefit of the disclosed technology is to young adults by preserving their natural teeth. Reduced retreatment and the need for tooth extractions provide significant savings to health care over patients' lives.

In some embodiments, the materials/device include a porous sponge scaffold (e.g., thermally crosslinked gelatin) and a hydrogel scaffold (e.g., in situ crosslinking methacrylated gelatin and heparin). The hydrogel scaffold can contain chemotactic, angiogenic, neurogenic, and/or immunomodulatory biofactors (e.g., Filgrastim (G-CSF, a recombinant human granulocyte colony stimulating factor sold under the name Neupogen, a.k.a. CSF3) and/or Epoetin alfa (EPO, a recombinant erythropoietin sold as Epogen). Other factors with chemotactic, angiogenic, neurogenic, and/or immunomodulatory effects include cytokines (interleukins (e.g. IL-4, IL-10, IL-13), lymphokines (e.g. granulocyte-macrophage colony-stimulating factor (GM-CSF, a.k.a. CSF2), a recombinant Sargramostim sold as Leukine), chemokines (e.g. CCL17, CCL22, SDF-1 (a.k.a. CXCL12)), growth factors (e.g. ANGs, BMPs, FGFs, Hedge Hogs, P1GFs, PDGFs, VEGFs, TGF-βs), neuroregulatory factors (e.g. BDNF, CGRP, NGF, norepinephrine, substance P, VIP), corticosteroids (e.g. dexamethasone, cortisone, prednisone, fluticasone propionate), and chemical agonist/antagonists (e.g. purmorphamine, tacrolimus, rapamycin). The hydrogel component can facilitate delivery of the biofactors by controlling the permeability to these factors and by directing binding them. Basic factors complex with positively charged hydrogel components (e.g. collagens, gelatins). Many of these factors have binding motifs for sulfated moieties on glycosaminoglycans that bind heparin, heparan sulfate, keratin sulfate, chondroitin sulfate and dermatan sulfate hydrogel components.

In other methods, some or all of the biofactors and drugs can be absent from the hydrogel scaffold and can be administered to the patients as needed separately from the implanted materials.

In one exemplary method, the materials can be implanted in a process as follows. In one step, after endodontic therapy the hydrogel material is injected into the treated canals. It is of low viscosity, filling complicated accessory roots that cannot be reached by conventional fillers such as gutta-percha. The hydrogel conforms to unshaped canals, which is compatible with alternate debridement/cleaning procedures such as aggressive and sonic/ultrasonic irrigation (i.e. fills unshaped canals). This leaves minimal to no gaps along canal walls which prevents bacterial invasion. In an optional subsequent step, the sponge scaffold can be placed into the root to further flow hydrogel into the canals and into the chamber for structural support (if needed). A tooth restoration procedure can then be performed to complete the process. The EPO and Filgrastim are exemplary materials selected from among various chemotactic, angiogenic/neurogenic and immunomodulatory factors that can alternatively be used with the disclosed technology.

The hydrogel and scaffold components can comprise naturally derived materials. Naturally derived materials can include decellularized matrices (e.g. Matrigel), proteins (e.g. collagens, gelatins, silk), glycoproteins (e.g. fibrin, fibrillins, fibronectin, SIBLINGs (e.g. bone sialoprotein, dentin sialoprotein, dentin phosphoprotein, DMP1, osteopontin), thrombospondins), elastins, proteoglycans, and/or glycosaminoglycans (e.g. alginate, chitosan, chondroitin sulfate, dextrans keratin sulfate, aggrecans, hyaluronan, heparin, heparan sulfate). The hydrogel and scaffold components may also comprise artificial materials, such as to further control the rate of cell migration and hydrogel swelling/contraction. Artificial materials can include a-hydroxyesters, poly(caprolactone), PIPAAm, poloxamers, p(ethylene glycol) (PEG), p(vinyl alcohol) (PVA), poly(acrylic acid) (PAA), and poly (vinylpyrrolidone). Artificial materials that do not alter local pH upon degradation are desirable to enhance cellular infiltration and tissue formation. These hydrogel and scaffold components can be crosslinked to form a hydrogels in situ using appropriate crosslinkers (e.g. tetrakis, genipin, transglutaminase), or via modification to provide active moieties, for example acrylated to render them crosslinkable via radicals generated with light (photocrosslinkable) and/or with persulfate salts (e.g., ammonium persulfate, potassium persulfate, sodium persulfate). Persulfate crosslinking rate can be controlled with addition of ascorbate.

The implanted materials/device can regenerate vital tissue in the root canals, can restore nerves and tooth sensation, and/or can restore vascularity and outward fluid flow through the dentinal tubules. The vital tissue may not be equivalent to native pulp tissue (e.g. nerve fibers are of different type, lack of odontoblasts). Restored sensation provides protection to extreme temperature and potential re-infection and further tooth damage. Restored vascularity provides interstitial fluid pressure that prevents bacterial migration into the tough through the dentin tubules by creating retrograde fluid flow.

Figure 1B:
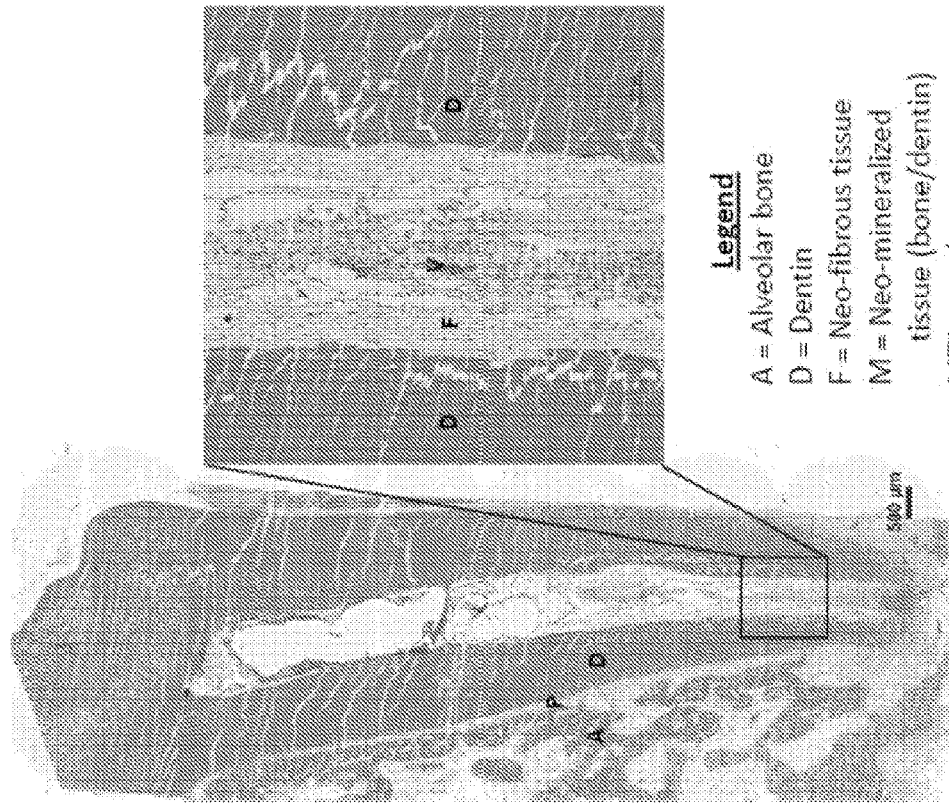
FIG. 1B shows a tooth root environment where a hydrogel material has been implanted without a sponge/scaffold material.
Figure 1C:
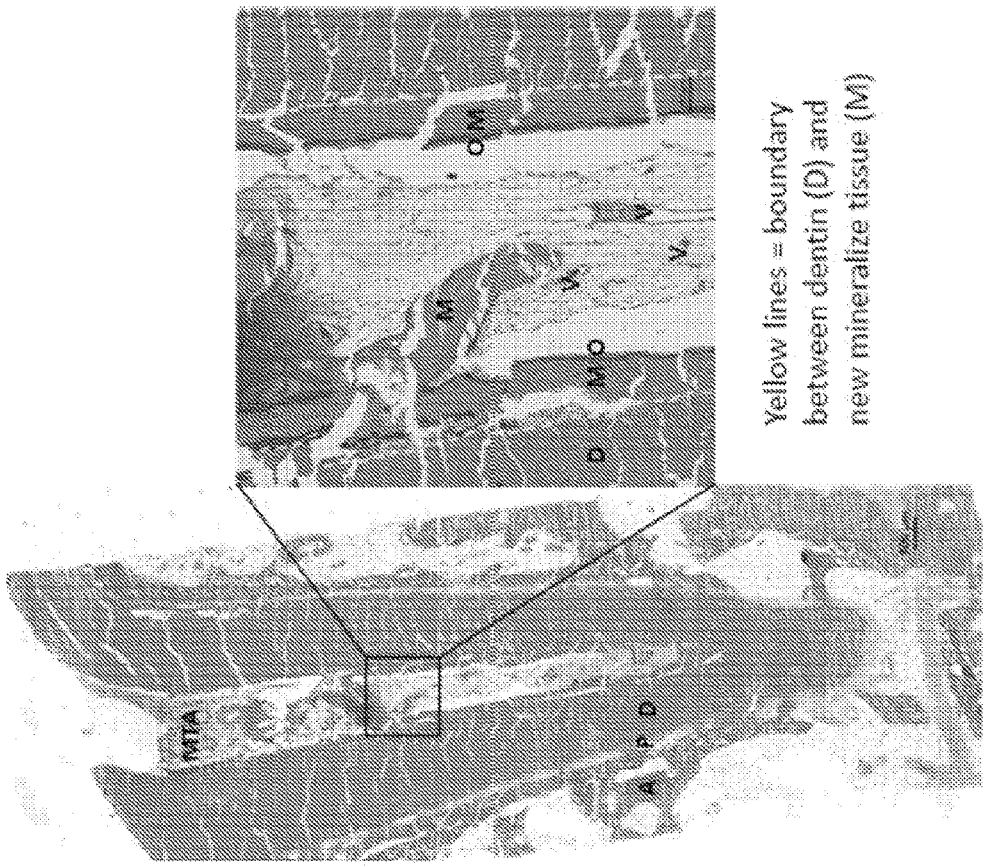
FIG. 1C shows a tooth root environment where a hydrogel material has been implanted with a sponge/scaffold material.

FIG. 1A illustrates devices and methods disclosed herein for regenerating vital tissue. These methods can include a pulpectomy and disinfection before implanting a hydrogel material with or without a sponge/scaffold material, and then allowing for vital tissue growth. The implantable material can include a porous sponge scaffold and an acellular hydrogel material that may or may not containing chemotactic, angiogenic, neurogenic, and immunomodulatory biofactors. FIG. 1B includes images of a tooth root environment where a hydrogel material has been implanted without a sponge/scaffold material. FIG. 1C includes images of a tooth root environment where a hydrogel material has been implanted with a sponge/scaffold material. For a patient, this technology helps to retain the natural tooth and surrounding natural tissues. Living pulp can help maintain obturation, can help prevent bacterial infiltration, and can help fight re-infection. This technology also helps to reduce the overall costs of treatment and avoids root-canal related complications.

Figure 2:
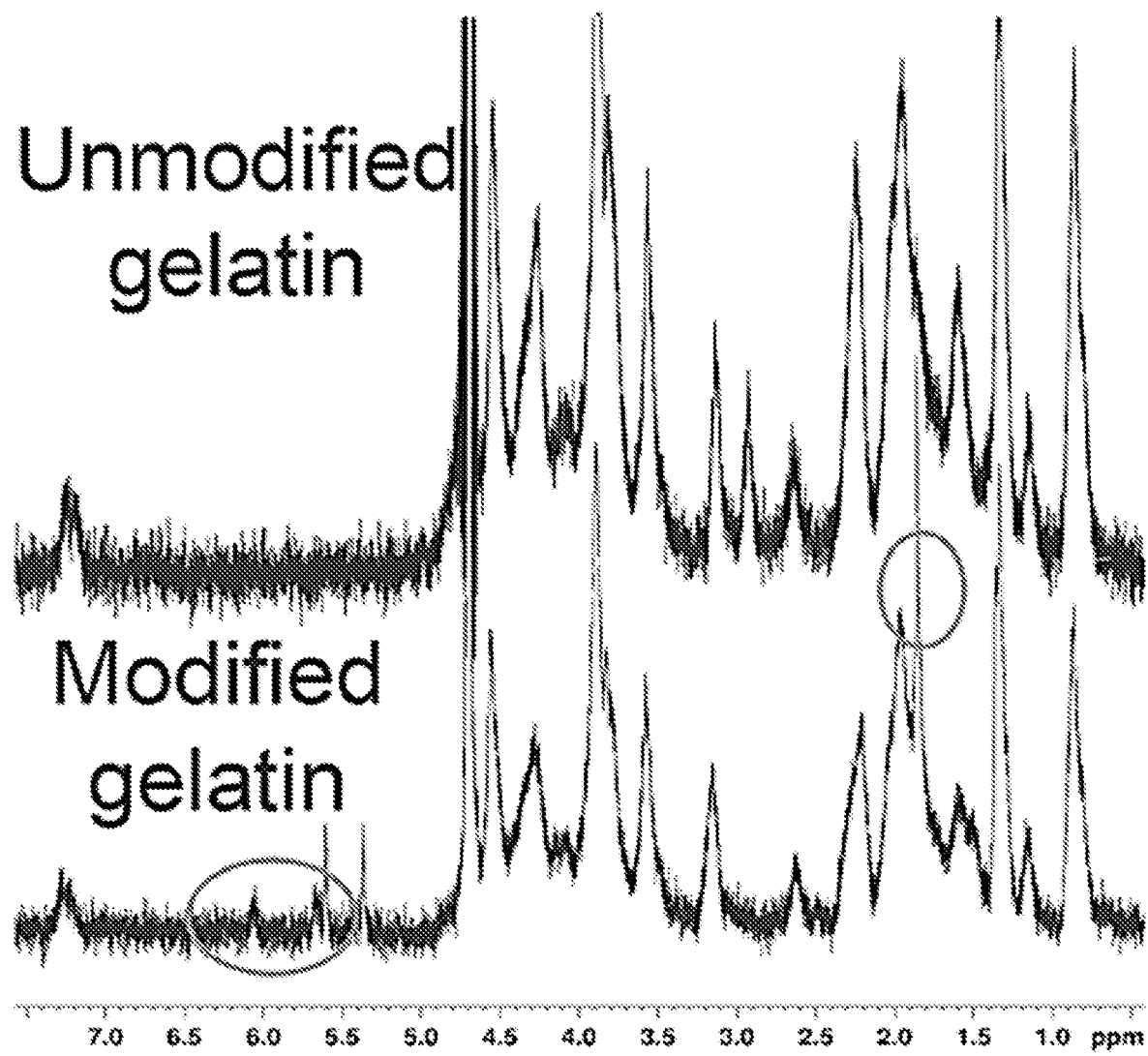
FIG. 2 shows nuclear magnetic resonance imaging (nMRI) of one polymer component (gelatin) of the hydrogel scaffold, demonstrating that the gelatin is methacrylated rendering it crosslinkable via radicals generated with light (photocrosslinkable) and/or with persulfates.

The hydrogel scaffold can include polymer components, such as gelatin and heparin, that can be methacrylated rendering them photocrosslinkable. Crosslinking can be performed using radiant energy systems, such as during photocrosslinking of resin systems, which provide control over the initiation of crosslinking. The acrylate moieties can also render the polymers crosslinkable without radiant energy, e.g. by persulfate chemistries, which can be useful for filling complicated canals and accessory canals. The disclosed hydrogel materials can readily flow into small canals to provide enhanced obturation compared to conventional materials such as gutta-percha. The hydrogel materials can also readily flow into the periapical space to fill irrigated abscess lesions. FIG. 2 shows a nuclear magnetic resonance image of gelatin, illustrating that the gelatin is methacrylated.

Figure 3:
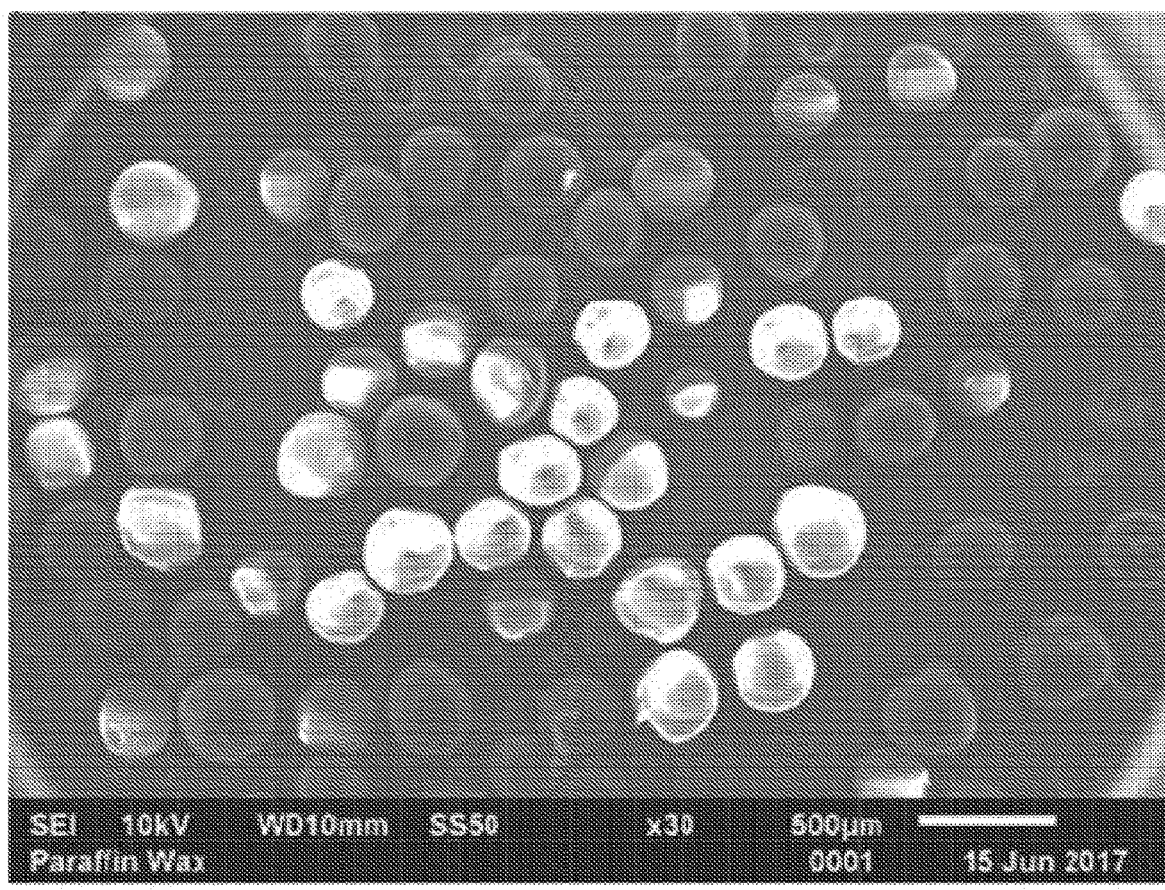
FIG. 3 is an image of porogens used in manufacturing sponge scaffold from polymers.
Figure 4:
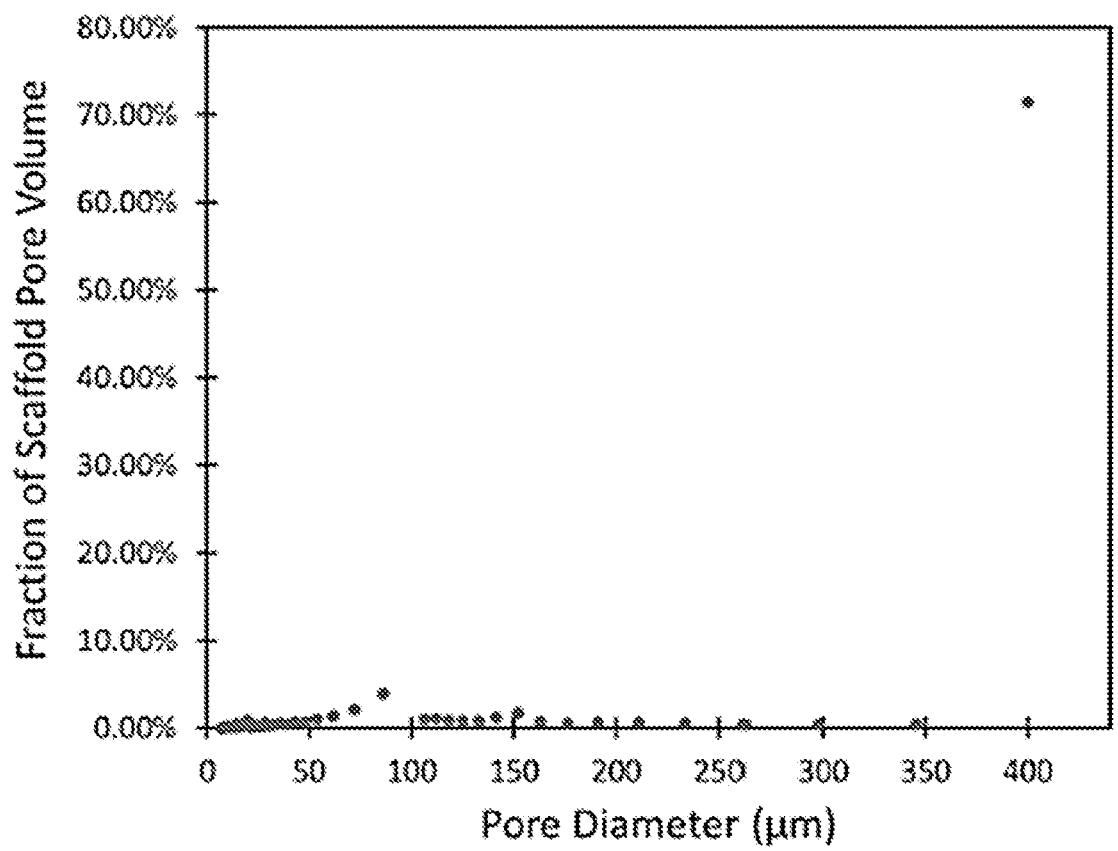
FIG. 4 is a plot that summarizes mercury porosimetry assays demonstrating that over 70% of the sponge scaffold pores are larger than 400 μm.
Figure 5:
FIG. 5 is a micro-computed tomography image of the internal structure of a sponge scaffold showing the aperture of interconnectivity between the pores.

The sponge scaffolds can be formed from polymers, and FIG. 3 is an image of porogens used in an exemplary process for manufacturing a sponge scaffold from polymers. FIG. 4 is a plot summarizing mercury porosimetry assays demonstrating that over 70% of the sponge scaffold pores are larger than 400 microns. FIG. 5 is a micro-computed tomography image of the internal structure of an exemplary sponge scaffold showing the aperture of interconnectivity between the pores. In some examples, the sponge is inserted following the hydrogel to create fluid flow to fill canals, and provides structural support, if necessary, for a conventional crown filler (e.g. mineral trioxide aggregate, MTA). The sponge scaffold can be made of gelatin, for example. In some embodiments, the sponge can be molded into tapered cone shapes of various sizes to correspond with dental file size, as in FIG. 1A. The sponge can also be shaped as a wafer that can be cut to fit the coronal pulp chamber, such as to be used for partial pulpectomy.

Figures 6A, 6B, 7:
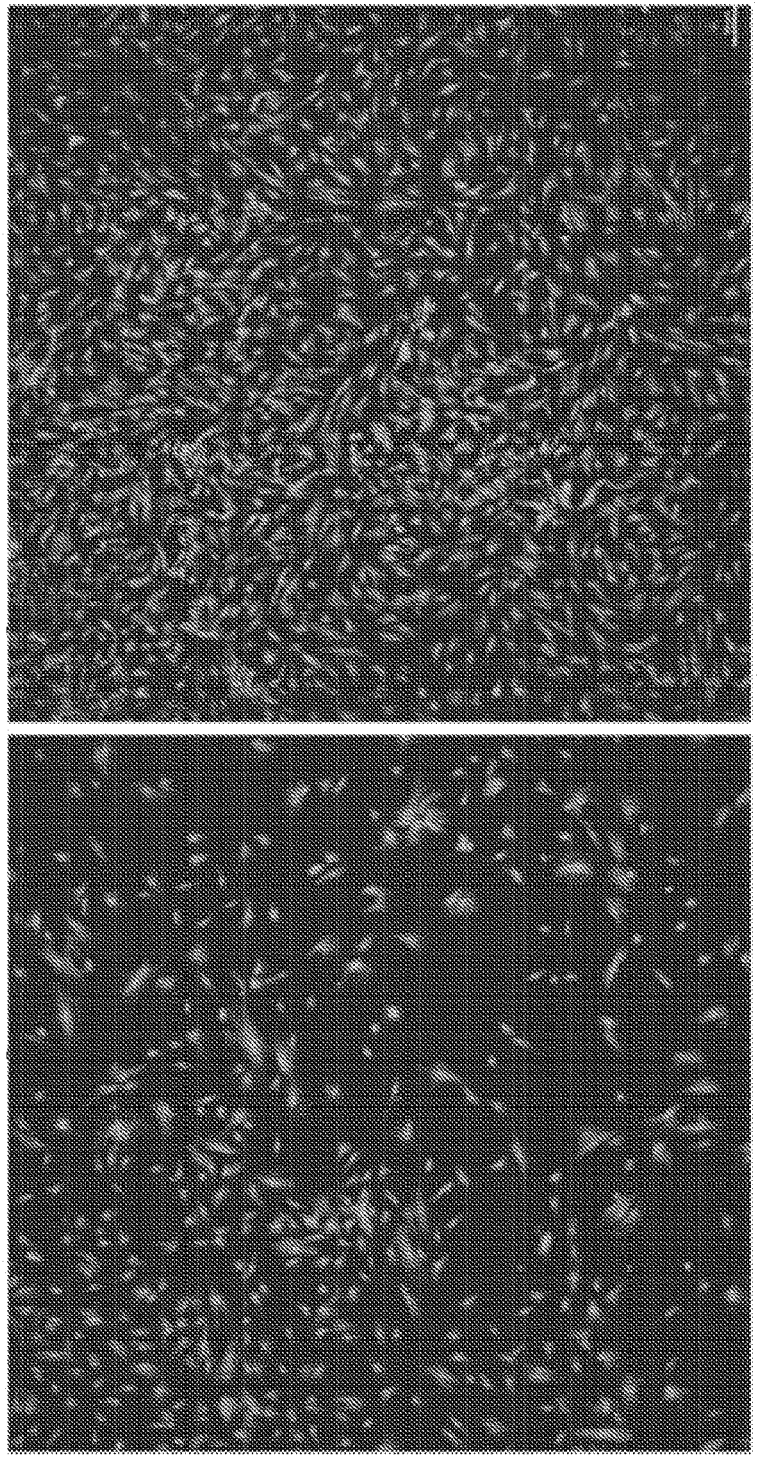
FIGS. 6A-6B are images that illustrate cytocompatibility of the biomaterials. In these images, the cells were subjected to coculture with the sponge scaffolds and no toxic effects were observed over 24 hours.
FIG. 7 is a table of mechanical properties of a sponge scaffold and a hydrogel.

FIGS. 6A and 6B are images that confirm cytocompatibility of the biomaterials used with the disclosed technology. In FIGS. 6A and 6B, the cells were subject to coculture with sponge scaffolds and no toxic effects were observed over 24 hours. FIG. 6A shows the cells at 1 hour, and FIG. 6B shows the cells at 24 hours. In these images, green represents live cells and red represents dead cells. Both images show all green cells and no red cells.

FIG. 7 is a table that lists mechanical properties measured for an exemplary hydrogel, an exemplary hydrated sponge, and an exemplary dry sponge, after irradiation sterilization, based on unconfined compression assays.

Figure 8:
FIGS. 8-10 are images that demonstrate root canal therapy (RCT) with the disclosed technology
Figure 9:
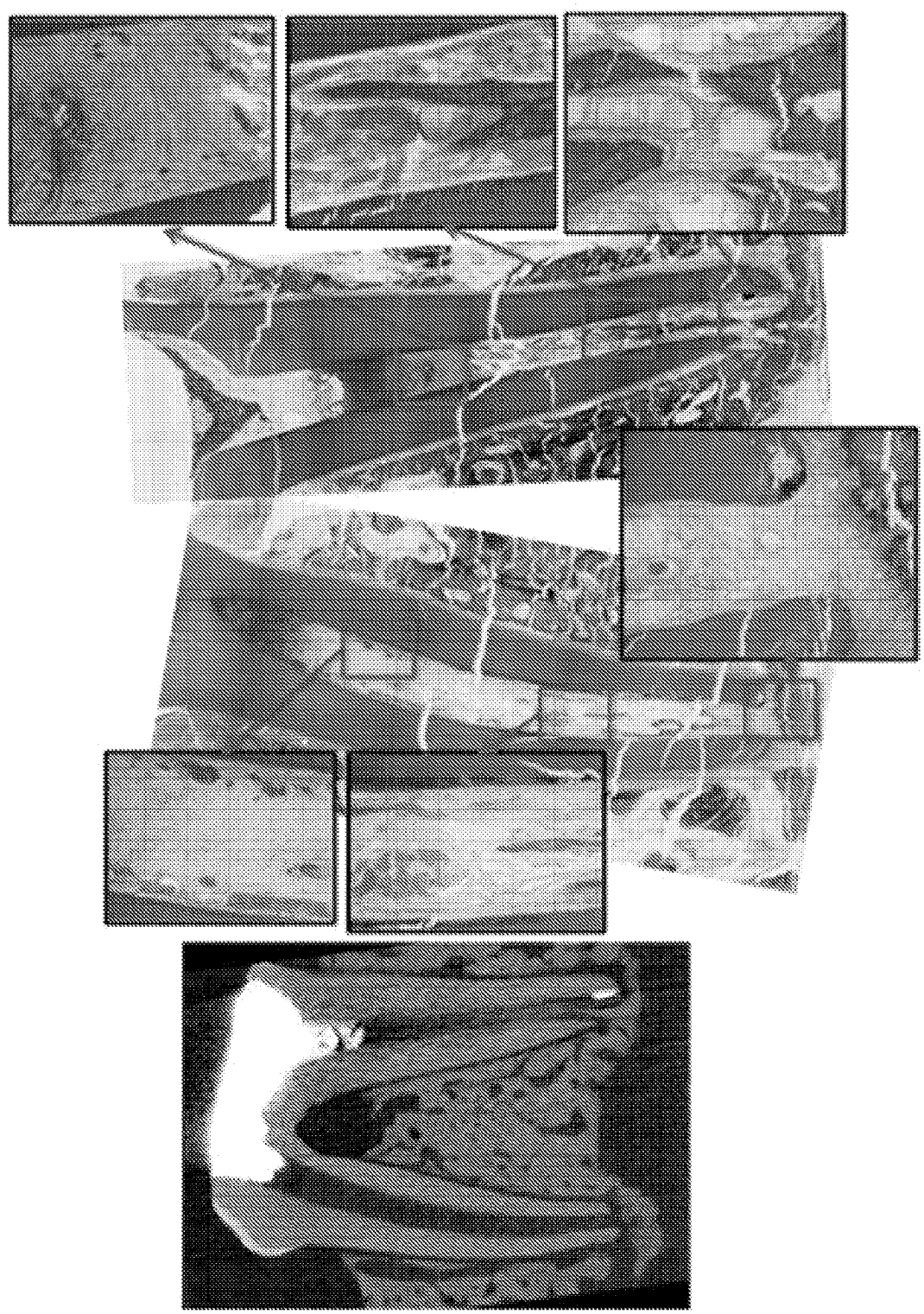
Figure 10:
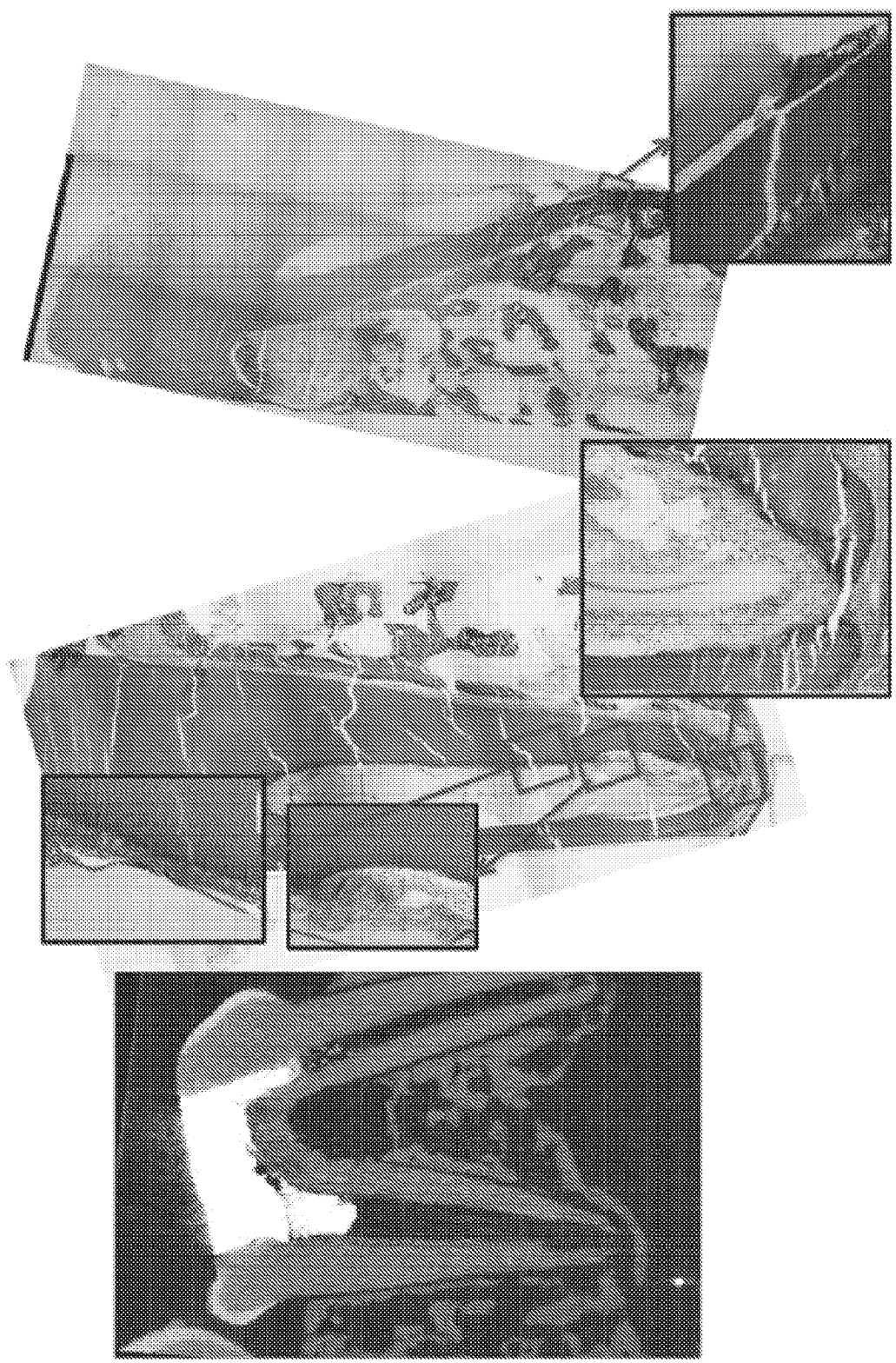

FIGS. 8-10 illustrate an exemplary root canal therapy treatment (RCT) with using the disclosed technology. In this example, RCT was performed on dog premolars and molars, including drilling through apex, and tissue analyzed after three months. The left-hand images are slice views of computed tomography (CT) images of a tooth, while the center and right-hand images are histological sections of the left and right root, respectively, stained with modified Mallory procedure. The histology images are rotated to align with the CT image.

As illustrated in FIG. 8, a conventional RCT treatment was initiated on a mature dog premolar (opening of the crown, removal of pulp tissue, canal shaping) and then the root canal was left unfilled and the opening sealed with a temporary filler (mineral trioxide aggregate, "MTA"). The left root canal was shaped through the apex (root tip) to serve as a no filler treatment control. The right root canal was not shaped through the apex to serve as a control for cellular infiltration and periapical injury and inflammation (no injury because the file did not protrude out of tooth root, and smaller accessory canals available for cell migration relative to the large filed canal on left root). Both roots show little cellular infiltration and regeneration. The left root demonstrates granulation tissue at the root apex and some cell migration and tissue formation along the dentin (left wall inside canal), but no regenerate tissue filling the canal. The right root also shows tissue along the dentin surface and some tissue filling the canal, but of low density. No blood vessels were observed in either root.

In the example shown in FIG. 9, the RCT treatment was initiated on a dog premolar and then the root canal filled with the disclosed hydrogel scaffold containing gelatin, heparin, and PEG (without the sponge scaffold) and the opening sealed with MTA. The hydrogel was loaded with purmorphamine Example factors are those with chemotactic, angiogenic, neurogenic, and immunomodulatory effects, such as G-CSF and EPO. Additional exemplary factors include FGF2, IL-4, NGF, tacrolimus, and VEGF. The device regenerated vital tissue within both roots throughout the canal up to the MTA sealer. Both roots show extensive regenerate tissue growth, including fibrous tissue, bone, and blood vessels, along the dentin walls and root canal proper. Residual hydrogel is evident, particularly in the left root.

In the example shown in FIG. 10, the RCT treatment was initiated on a dog premolar, and then the root canal filled with the disclosed hydrogel scaffold (without the sponge scaffold) and the opening sealed with MTA. In this example, the hydrogel was not loaded with the factors having chemotactic, angiogenic, neurogenic, and immunomodulatory effects, other than the hydrogel material itself. The result shows some regenerate tissue formation within the left root, namely along the dentin walls akin to the control group, but with more regenerate tissue along the walls. The hydrogel is still present in the roots, and shows less resorption than in the device group. The right root shows less cellular infiltration along the dentin.

Figure 12:
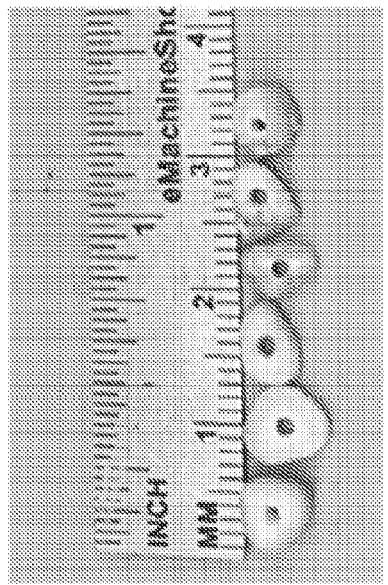
FIG. 12 shows 2 mm thick slices of devitalized human tooth root channels.
Figure 14:
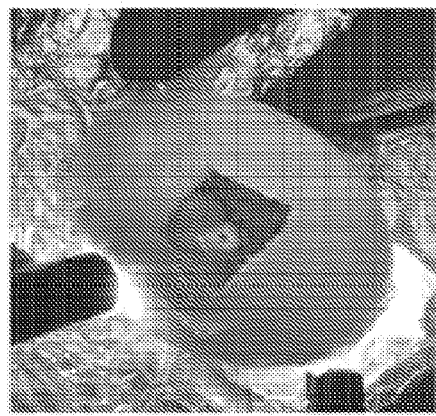
FIG. 14 shows a tooth slice filled with sponge/hydrogel scaffold being cultured on a CAM.
Figure 11:
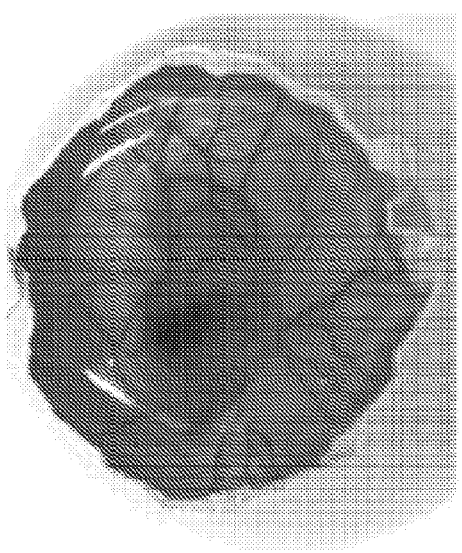
FIG. 11 shows a chick chorioallantoic membrane (CAM).
Figure 13:
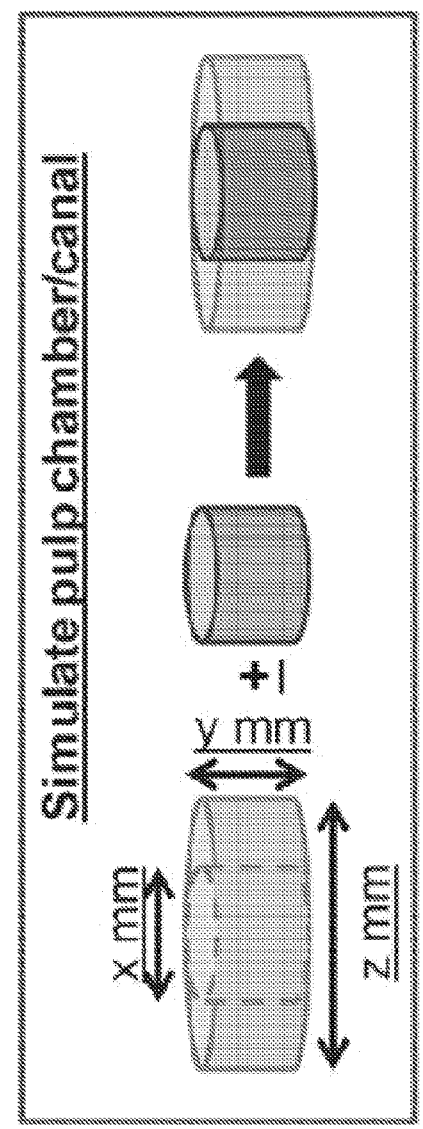
FIG. 13 illustrates a sponge or hydrogel scaffold placed in the root canal openings of the tooth slices.

FIGS. 11-14 illustrate an application of the disclosed technology composition using a model where tooth slices and/or the implanted materials are cultured on a chick chorioallantoic membrane (CAM), an example of which is shown in FIG. 11. The teeth slices were devitalized and sterilized (sodium hypochlorite) but not activated (no EDTA treatment). As shown in FIG. 12, human teeth were devitalized, the root channels shaped, and the roots cut into 2.0 mm thick slices. As illustrated in FIG. 13, these hollow slices were filled with either the sponge or hydrogel scaffold components and grown for seven days on a CAM (as shown in FIG. 14).

Figure 16:
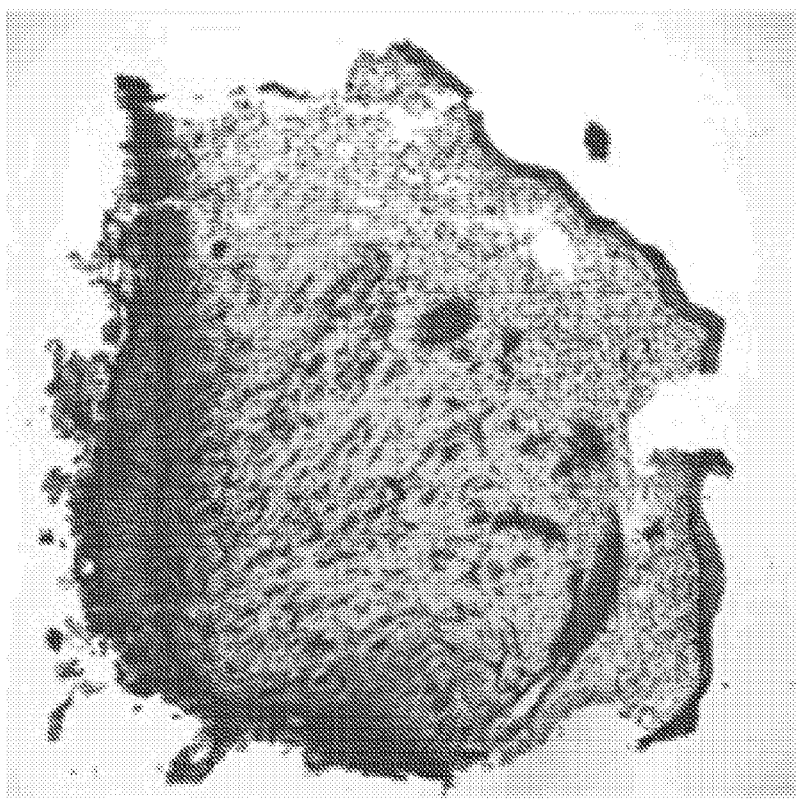
FIG. 16 is an image of a hydrogel scaffold that was loaded with cytokines/growth factors and cultured on the CAM for one week. In this image, extensive cellular infiltration, fibrous tissue formation, and angiogenesis is visible.
Figure 15:
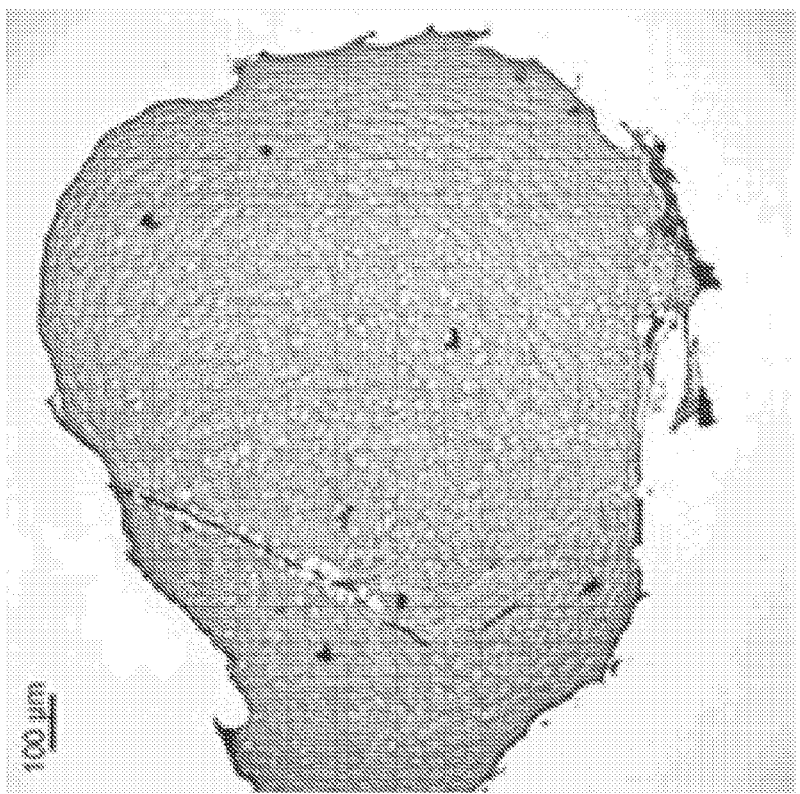
FIG. 15 is an image of a hydrogel scaffold that was not loaded with cytokines/growth factors and cultured on the CAM for one week.

As illustrated in FIGS. 15 and 16, clear differences are visible between hydrogel scaffolds grown with and without factors having chemotactic, angiogenic, neurogenic, and immunomodulatory effects. The hydrogel scaffold in FIG. 15 was not loaded with factors, while the hydrogel in FIG. 16 was loaded with G-CSF and EPO factors before placement on the CAM. Extensive cellular infiltration, fibrous tissue formation, and angiogenesis is evident in FIG. 16 (with the cytokines/growth factors). FIG. 15 shows cellular infiltration and fibrous tissue only on the periphery (i.e. between the hydrogel and dentin walls).

Figures 17, 18:
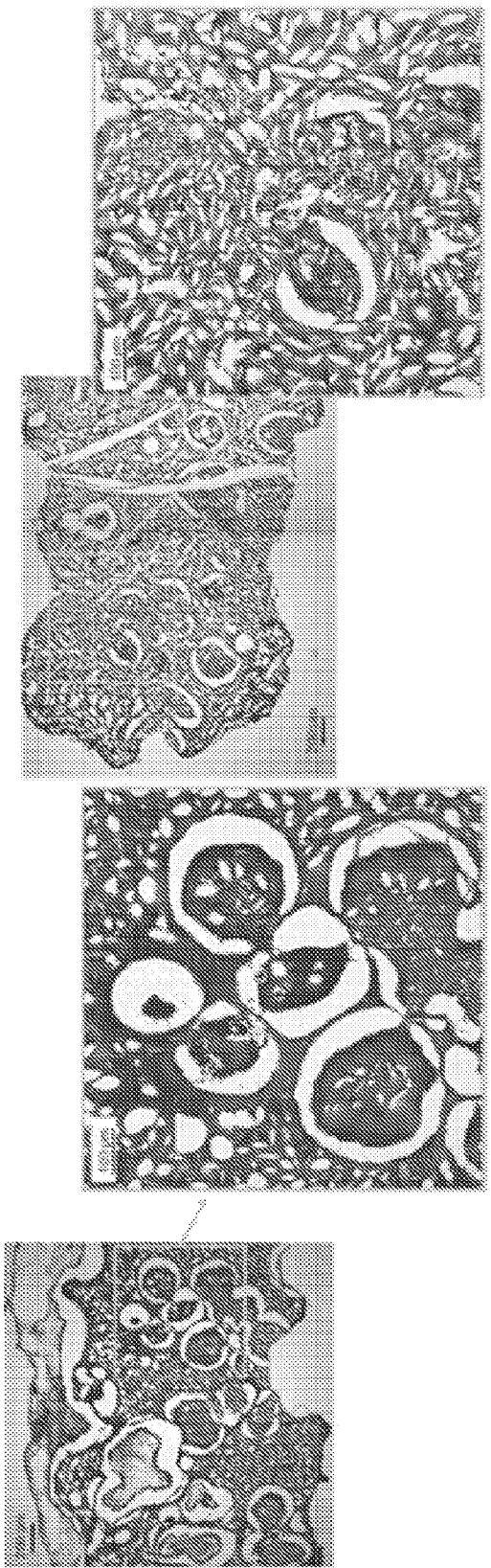
FIGS. 17 and 18 are images of sponge scaffolds that are cut into cylinders and inserted into the root slice holes.

FIGS. 17 and 18 illustrate examples where sponge scaffolds were cut into cylinders and inserted into the root slice holes. FIG. 17 shows sponges doped with buffered saline solution without cytokines/growth factors, while FIG. 18 shows sponges doped with saline solution containing cytokines/growth factors. Little cellular infiltration is evident without cytokines/growth factors (FIG. 17, top side was in contact with the CAM), while angiogenesis and greater cellular infiltration occurs with G-CSF and EPO (FIG. 18, bottom side was in contact with the CAM). The hydrogels show enhanced tissue infiltration compared to the sponge scaffolds.

FIGS. 1B and 1C illustrate exemplary RCT using the disclosed technology, where the roots were filled with disclosed hydrogel (8% w/v) containing gelatin and heparin at 3 to 2 mass ratio. In these examples, the hydrogel was not loaded with the factors having chemotactic, angiogenic, neurogenic, and immunomodulatory effects, other than the hydrogel material itself. In this example, the dogs were treated with 2 mg/kg dexamethasone one time on the day before the RCT. The RCT was performed on the dog premolars and molars, including drilling through apex, and tissue analyzed after three months. The stain is Goldner's trichrome. FIG. 1B includes images of a tooth root environment where the hydrogel material has been implanted without a sponge/scaffold material. FIG. 1C includes images of a tooth root environment where a hydrogel material has been implanted with a sponge/scaffold material. The drug-free hydrogel promoted migration of progenitor cells from the peri-apical space, stimulated angiogenesis, and regenerated fibrous and mineralized tissue. The mineralized tissue covered the shaped canal walls, which was itself was covered with unmineralized predentin/osteoid. Regeneration occurred up to the MTA sealer. No infections or dystrophic calcification occurred in treated teeth. For a patient, this technology helps to retain the natural tooth and surrounding natural tissues. Living pulp can help maintain obturation, can help prevent bacterial infiltration, and can help fight re-infection. This technology also helps to reduce the overall costs of treatment and avoids root-canal related complications.

The disclosed technology can be an acellular therapy, utilizing the bioactive factors to promote infiltration of endogenous cells from the periapical space of the patient into the tooth roots, rather than relying in the implantation of cellular material into tooth roots. Promoting infiltration of endogenous cells from the patient into the tooth roots results in improved vital tissue regeneration in the pulp chamber and canals, and the regenerated tissue is better situated for long-term vitality because it is a product of the patient's own endogenous cells as opposed to the product of implanted cells sourced from elsewhere. The disclosed acellular therapy can also provide used as an "off-the-shelf" treatment.

The disclosed technology can include particular methods for preparation of the tooth. For example, in some methods, the apex of the tooth has to be opened to provide a conduit for cellular infiltration to occur. This can be a challenge because the dental professional can easily insert a file or other conventional tool too far into the alveolar bone such that a hyper-acute inflammatory process in engendered. In orthograde endodontic treatment (non-surgical, e.g., access to canals is via the tooth occlusal surface), the canal is cleaned in the normal fashion with files and the apex is opened with a rotary or hand held endodontic file. The anatomic apex is identified with an electronic apex locator and the anatomic apex is opened to a size 50 file (0.5 mm). The typical preparation is 0.5-1.0 mm short of the anatomic apex or a small preparation 0.2-0.25 mm just to the anatomic apex. The voids are irrigated with a 1% solution of NaCl for disinfection and then canals may be treated with EDTA (e.g. 17% w/v) to release growth factors from the dentin prior to placement of the hydrogel and sponge. The hydrogel and sponge are then placed into the canal and periapical space if needed. When treating teeth with retrograde endodontic treatment (surgical, e.g., for treatment of persistent infections, broken tools left within root, large apical abscess), the tooth canal is cleaned in the normal fashion using files, a full thickness flap is raised to access the apical abscess, the abscess is curetted, and the apical third of the root removed. This opens the apex and removes the infected root surface and abscessed tissue. The canal is irrigated and treated. Then the hydrogel and sponge are placed into the canal and into the osseous defect, and the flap closed with suture.

Moreover, with the disclosed technology, the flowable hydrogel and sponge insertion procedures can fill the tooth root canals particularly well, including unshaped canals, minimizing spaces where infection can flourish and maximizing tissue ingrowth and regeneration. The disclosed technology also has the advantage of being able to regenerate tissue with viable nerves that can respond to hot/cold and pressure sensations, which helps protect the tooth from further damage.

In some of the herein disclosed methods, chemotactic, angiogenic, neurogenic, and immunomodulatory biofactors and/or other drugs can be included in and delivered from the implanted hydrogel/scaffold. As an alternative, or in addition, in some methods some or all of these biofactors/drugs can be excluded from the implanted hydrogel/scaffold. In some such methods, these biofactors/drugs can be administered to the patient separately from the hydrogel/scaffold. For example, in some methods, a brief immunosuppressive regimen can be administered to a patient pre-op, which can have a potentiating effect on regeneration of vital tissue. In some methods, all drugs including anti-inflammatories can be absent from the hydrogel, and instead the method can include delivering an immunosuppressive regimen of dexamethasone or other corticosteroid medication, and/or other drugs, to the patient separate from the hydrogel.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics, materials, values, moieties, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically or chemically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A method of regenerating vital tooth tissue in situ after endodontic therapy, comprising:
   forming an opening in a tooth in a patient and removing native pulp from a root canal of the tooth;
   after removing the native pulp from the root canal, introducing a hydrogel scaffold into the root canal, and
   sealing the opening after introducing the hydrogel scaffold into the root canal; and wherein:
   the hydrogel scaffold comprises an acellular heparin and gelatin hydrogel scaffold;
   the gelatin:heparin mass ratio is about 3 to 2;
   the hydrogel scaffold has sufficiently low viscosity such that it flows into smaller accessory canals of the root canal and fills substantially an entire space within the root canal, and thereby provides obturation to block blood from entering the root canal;
   the hydrogel scaffold comprises a collagen-derived amino acid polymer that contains cell-binding motifs and is biodegradable via enzymatic degradation, and a sulfated polysaccharide that is anionic and is biodegradable via enzymatic degradation; and
   the collagen-derived amino acid polymer comprises gelatin and the sulfated polysaccharide comprises heparin.

2. The method of claim 1, wherein the hydrogel scaffold comprises chemotactic, angiogenic, neurogenic, and immunomodulatory biofactors that cause infiltration of endogenous cells from the patient into the root canal.

3. The method of claim 1, wherein the hydrogel scaffold is free of drugs and biofactors other than the hydrogel scaffold itself, and the method comprises:
   administering, separate from the hydrogel scaffold, chemotactic, angiogenic, neurogenic, and immunomodulatory biofactors that inhibit inflammation or promote infiltration of endogenous cells from the patient into the root canal.

4. The method of claim 1, wherein the hydrogel scaffold is carried within a sponge scaffold and the sponge scaffold is introduced into the root canal with the hydrogel scaffold.

5. The method of claim 1, further comprising treating the patient with an anti-inflammatory drug regimen.

6. The method of claim 5, wherein treating the patient with the anti-inflammatory regimen comprises treatment with corticosteroids or non-steroidal anti-inflammatory drugs.

7. The method of claim 1, further comprising performing a tooth restoration procedure on the tooth after the hydrogel scaffold is introduced and the opening is sealed.

8. The method of claim 1, further comprising opening an apex of the tooth to provide a conduit for cellular infiltration to occur.

9. The method of claim 1, wherein the hydrogel scaffold fills periapical space of an abscessed root.

10. The method of claim 1, wherein the hydrogel scaffold comprises in situ crosslinking methacrylated gelatin and heparin.

11. The method of claim 2, wherein the hydrogel scaffold comprises drug binding moieties.

12. The method claim 4, wherein the sponge scaffold comprises thermally crosslinked gelatin.

13. The method of claim 2, wherein the biofactors comprise chemokines, cytokines, lymphokines, growth factors, neuroregulatory factors, immunomodulatory, or chemical agonists.

14. The method of claim 2, wherein the biofactors comprise corticosteroids, purmorphamine, Filgrastim or Epoetin alfa.

15. The method of claim 2, wherein the biofactors suppress an acute inflammatory reaction caused by endodontic therapy in the periapical space.

16. The method of claim 1, wherein the hydrogel scaffold expands within the root canal to fill substantially the entire space within the root canal.

17. The method of claim 1, wherein the heparin and gelatin are about 8% w/v of the hydrogel scaffold.

18. The method of claim 1, wherein the heparin is covalently crosslinked to the hydrogel scaffold.

* * * * *